(12) United States Patent
Glenn

(10) Patent No.: US 8,425,476 B2
(45) Date of Patent: Apr. 23, 2013

(54) STABILIZED ELONGATE IMPLANTABLE VASCULAR ACCESS DEVICE

(75) Inventor: Bradley J. Glenn, Oneida, WI (US)

(73) Assignee: Stealth Therapeutics, Inc., Madison, WI (US)

( * ) Notice: Subject to any disclaimer, the term of this patent is extended or adjusted under 35 U.S.C. 154(b) by 0 days.

(21) Appl. No.: 13/332,663

(22) Filed: Dec. 21, 2011

(65) Prior Publication Data

US 2012/0088977 A1    Apr. 12, 2012

Related U.S. Application Data

(63) Continuation of application No. 12/080,981, filed on Apr. 7, 2008, now Pat. No. 8,083, 723.

(60) Provisional application No. 60/907,526, filed on Apr. 5, 2007.

(51) Int. Cl.
  *A61M 37/00* (2006.01)
(52) U.S. Cl.
  USPC ............. 604/288.01; 604/288.02; 604/288.04

(58) Field of Classification Search ............ 604/288.01–288.04, 105, 106, 175; 600/201
See application file for complete search history.

(56) References Cited

U.S. PATENT DOCUMENTS

| 7,708,722 B2 * | 5/2010 | Glenn | 604/288.02 |
| 8,083,723 B2 * | 12/2011 | Glenn | 604/288.01 |

* cited by examiner

*Primary Examiner* — Kevin C Sirmons
*Assistant Examiner* — Brandy C Scott
(74) *Attorney, Agent, or Firm* — Heisler & Associates

(57) ABSTRACT

A vascular access port is described that is elongate in form. A distal end is coupled to a tube which leads into a body lumen. A proximal end has a head thereon with a septum which can be repeatedly penetrated by a needle and reseal, for repeated administration of medications or other compositions through the port and into the body of the patient. A wing is attached to the body that has two positions including a streamlined first position for implantation and a wider second position for stabilization of the port after implantation. A stay is preferably also provided to abut the wing when in the second position to keep the wing in the second position when fully deployed.

22 Claims, 5 Drawing Sheets

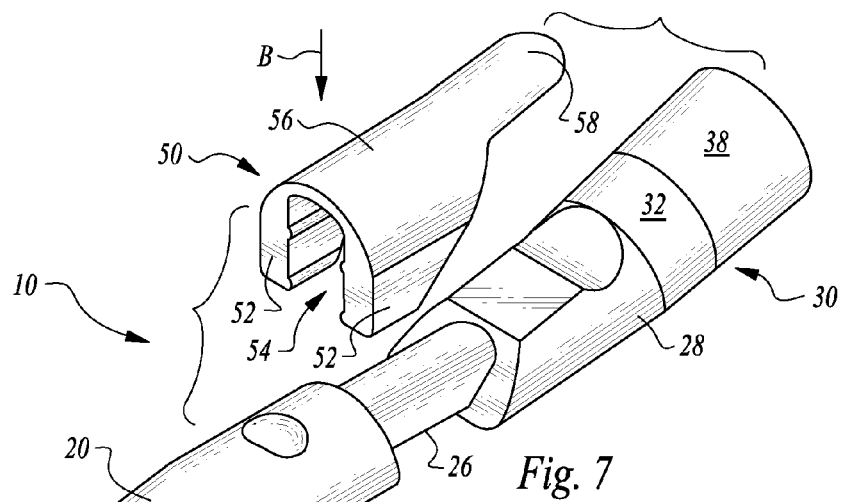
Fig. 7
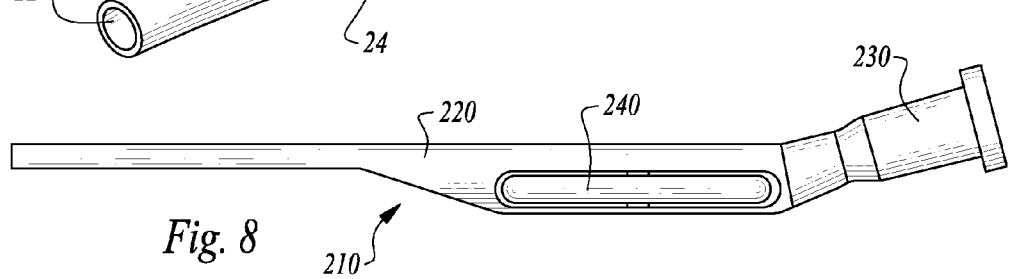
Fig. 8
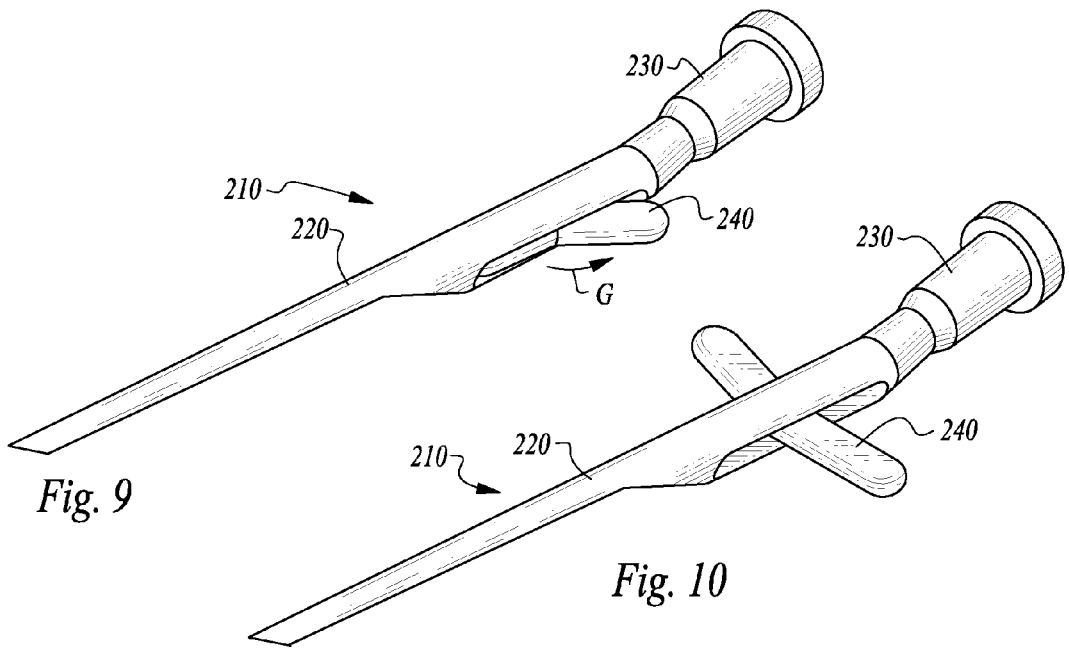
Fig. 9
Fig. 10

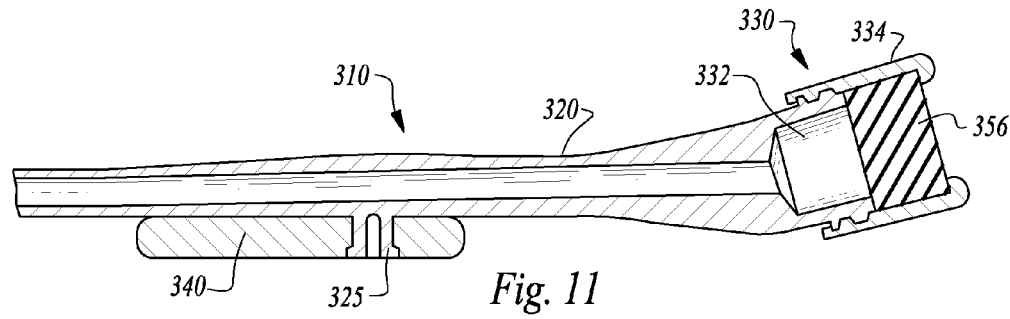
Fig. 11
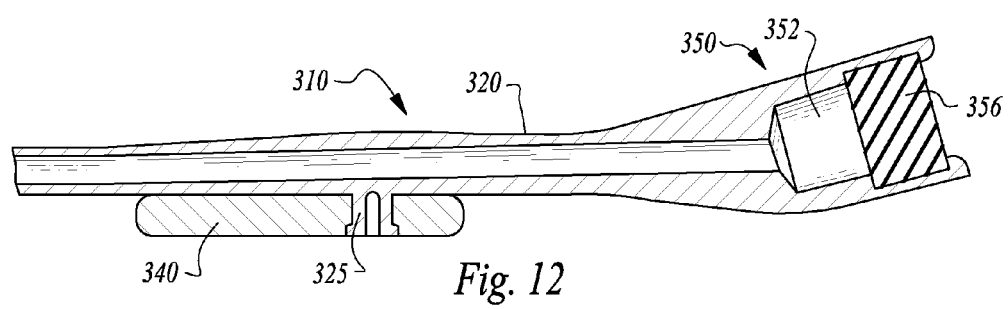
Fig. 12
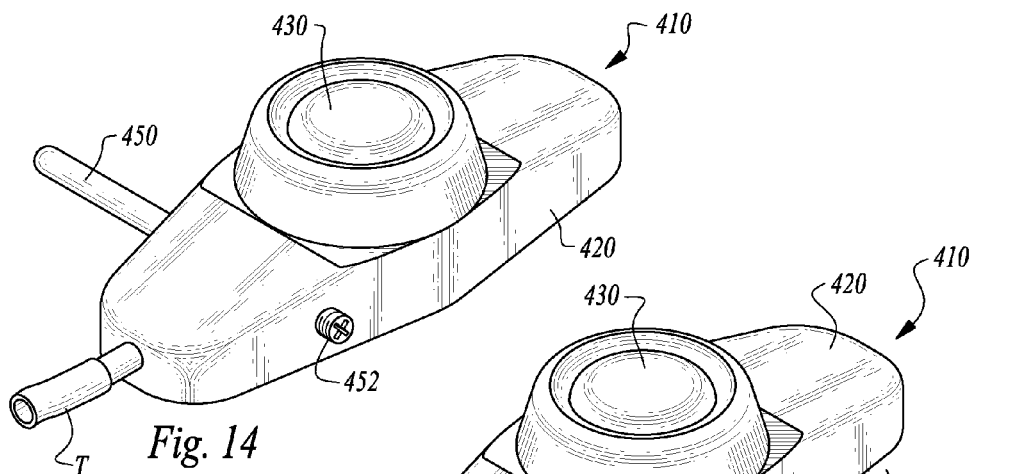
Fig. 14
Fig. 13

STABILIZED ELONGATE IMPLANTABLE VASCULAR ACCESS DEVICE

CROSS-REFERENCE TO RELATED APPLICATIONS

This application is a continuation of U.S. patent application Ser. No. 12/080,981, filed on Apr. 7, 2008 now U.S. Pat. No. 8,083,723 which claims benefit under Title 35, United States Code §119(e) of U.S. Provisional Application No. 60/907,526 filed on Apr. 5, 2007.

FIELD OF THE INVENTION

The following invention relates to implantable medical devices which are implanted subcutaneously and which interface with a body lumen, such as a vascular structure, and which can be themselves accessed by a needle through the skin for delivery of medications and other preparations into the vascular system of the patient. More particularly, this invention relates to vascular access devices, also referred to as ports, which are implanted subcutaneously and which include structures to help maintain the port in a stable position at the subcutaneous implantation site.

BACKGROUND OF THE INVENTION

Subcutaneously implanted vascular access devices, or ports, have been used for many years to provide long term vascular access in patients that require frequent or periodic therapeutic infusions or blood draws. Currently, ports generally have a body which contains a chamber accessible by a self-sealing septum and an outlet which is connected to a catheter which is placed into the vascular system. The base of the port is a generally flat side of the port which is intended to lie against the body, so the septum is generally oriented toward the skin surface. Many variations are possible. The septum may be convex or concave. The body may be plastic, metal or a combination of materials. The septum may be directly opposite the base, or may be angled relative to the base.

In current practice, the port is implanted into a subcutaneous pocket during a minor surgical procedure. One limitation to the development of smaller profile ports is the problem of port stability within the body after being placed. Ports in use currently may have a propensity to flip-over within the body if not sutured in place, rendering them inaccessible because the septum is facing down rather than up. The smaller the port, the greater the propensity to flip-over, and the harder it is to suture the port in place due to the smaller incision and smaller working pocket within which to suture. Thus, there is a need for a method to increase port stability while minimizing port implantation profile.

One such prior art port with a body that exhibits a generally elongate form and with an associated elongate septum is described in U.S. Pat. No. 6,213,973. While such a configuration does allow for a slightly minimized incision size, this prior art access port is not stabilized and is thus susceptible to "flipping-over" or otherwise rotating into an undesirable position.

Accordingly, a need exists for a vascular access port which provides both the benefit of stability once implanted and a small profile for insertion through a small incision, with the vascular access port being sufficiently small to allow for a minimization of size of the access port and other negative attributes associated with provision of such a vascular access port for the patient.

SUMMARY OF THE INVENTION

This invention provides a vascular access port which is elongate in form and adapted to be implanted subcutaneously. The port includes an elongate body with one end adapted to be placed in communication with a vascular structure or other body lumen, such as through an outlet tube. The other end of the body includes a head which can be accessed from outside of the skin and penetrated by a needle for injection of a medication or other substance into the body in communication with the outlet tube, for delivery to the vascular system of the patient. This head includes a septum which can be penetrated by the needle and which reseals after the needle has been removed.

A wing is provided on the body which is adjustable between two positions including a first position and a second position. The first position is more streamlined and closer to other portions of the body of the port. The second position places the wing with tips thereof extending further from the body than with the first position. In this second position, the wing is positioned so that rotation of the elongate body about a long axis thereof is resisted. Thus, the wing acts to stabilize the port and keep it in position within the subcutaneous implantation site. The port also preferably includes a stay which can be readily manipulated to a position where it keeps the wing in the second position after it has been moved into the second position. The port is implanted through an incision in the skin when the wing is in the first position so that a smaller incision can be utilized and implantation is simplified due to the smaller cross-section of the port when the wing is in the first position. After the port has been implanted to the desired implantation site, the wing is then adjusted to the second position to configure the port for maximum stabilization. A stay can then optionally be utilized to keep the wing in this second position.

OBJECTS OF THE INVENTION

Accordingly, a primary object of the present invention is to provide a port which can be accessed at a subcutaneous implantation site multiple times for delivery of medications or other compositions to a vascular structure or other body lumen.

Another object of the present invention is to provide a subcutaneous access port which is easy to implant.

Another object of the present invention is to provide a subcutaneous access port which is stable once implanted, and resists rotation, or other displacement.

Another object of the present invention is to provide a subcutaneous access port which has a form which changes in size from a size smaller than an incision during implantation to a size larger than at implantation after full deployment.

Another object of the present invention is to provide a subcutaneous access port which can be easily found and injected thereinto, but which is not particularly noticeable through the skin when not being used.

Another object of the present invention is to provide a method for reliably and repeatedly delivering medications and other compositions into the vascular system of a patient utilizing a subcutaneous vascular access port.

Other further objects of the present invention will become apparent from a careful reading of the included drawing figures, the claims and detailed description of the invention.

BRIEF DESCRIPTION OF THE DRAWINGS

FIG. 7 is a perspective view of portions of the port of FIG. 1 with the snap stay thereof shown exploded away from a body thereof before utilization of the snap stay to hold a wing thereof in position, and with the wing removed to clearly show an axle upon which the wing is supported.

FIGS. 8-10 are various views of a second alternative port with an enclosed wing that can pivot from a first more streamlined position to a second deployed position.

FIGS. 11 and 12 are side elevation full sectional views of two variations of a third alternative port, and illustrating variations for a head of the vascular access port of this invention.

FIGS. 13 and 14 are perspective views of a fourth alternative port utilizing a removably attachable threaded wing on a less elongate port than other embodiments shown herein.

DESCRIPTION OF THE PREFERRED EMBODIMENT

Figure 1:
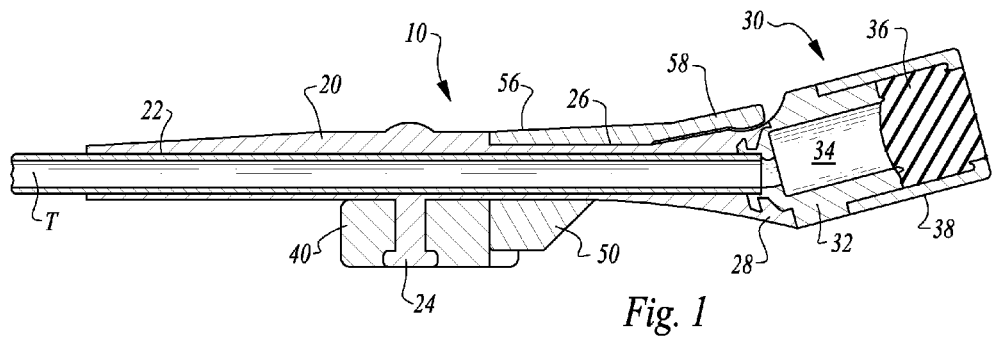
FIG. 1 is a side elevation full sectional view of the port of this invention according to a preferred embodiment.

Referring to the drawings, wherein like reference numerals represent like parts throughout the various drawing figures, reference numeral 10 is directed to a vascular access port which can be implanted subcutaneously (FIG. 6) with a tube T or other structure accessing a body lumen L, such as a vascular structure. The port 10 can then be accessed through the skin S, such as by a needle N, for delivery of medications or other compositions into the various internal structures of the patient. This invention is directed to variations on a vascular access port described in U.S. patent application Ser. No. 11/651,770, filed on Jan. 9, 2007, the contents of which are incorporated herein by reference in their entirety.

Figure 6:
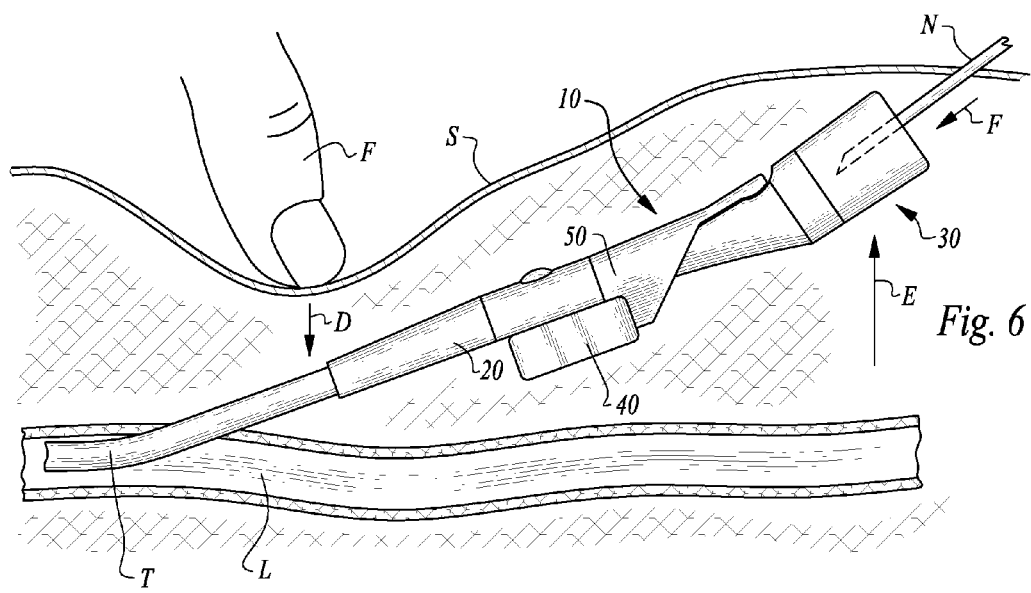
FIG. 6 is a side elevation view of the port of FIG. 1 at the implantation site and illustrating a method for manipulating the port to enhance accessibility to the head of the port with a needle.

In essence, and with particular reference to FIGS. 1-3 and 7, basic details of this invention are described, according to a preferred embodiment. The port 10 includes an elongate body 20 having a hollow conduit 22 within an interior thereof extending between ends of the body 20. One of the ends supports a tube T which then can access the desired internal body structure to which the port 10 provides access. The other end supports a head 30 thereon. The head 30 is selectively accessible, such as through a septum 36, which can be repeatedly penetrated by a needle N and reseal after needle N removal (FIG. 6).

The body 20 also includes a wing 40 thereon. This wing 40 is rotatably mounted to the body so that the wing 40 can rotate between a first position and a second position. The first position has the wing generally aligned with a long axis of the body 20. The second position has the wing pivoted to have the wing extending at least partially lateral to a long axis of the body 20. In the second position, the wing 40 provides enhanced stability for the port 10 to prevent the port 10 from undesirable movement while in the subcutaneous implantation site. A snap stay 50 is preferably provided which can snap onto the body 20 after the wing 40 has been rotated. This snap stay 50 keeps the wing 40 in the second position. Five alternative ports are also described herein which teach various different variations on the stabilized vascular access ports, illustrating a range of vascular access devices within the scope of this invention.

More specifically, and with continuing reference to FIGS. 1-3 and 7, particular details of the body 20 of the port 10 are described, according to the preferred embodiment. The body 20 is an elongate rigid structure having a hollow interior defining a conduit 22 extending between a distal end and a proximal end of the body 20. This conduit 22 preferably has a tube T accessing at least the distal end, and preferably passing entirely through the conduit 20 as a sort of sleeve within the conduit 22 of the body 20. The tube T extends onto a body lumen L, such as a vascular structure (most typically part of the venous system of the patient), to act as an outlet tube for delivery of fluids routed into the port 10 through the head 30 as described below. The body 20 preferably has a cross-sectional size which is significantly smaller than a longitudinal length of the body 20, such as at least five times smaller in cross-sectional width than in longitudinal length. The body 20 is preferably streamlined so that it can be inserted along a long axis through a small incision to a subcutaneous implantation site.

The body 20 includes an axle 24 thereon, and preferably extending perpendicular to the long axis of the body 20 in a vertical downward direction. This axle 24 provides a support upon which the wing 40 can be rotatably mounted as described in detail below. The body 20 can also include other structures near the axle 24 to streamline a contour of the body 20 around the axle 24 and the associated wing 40, particularly when the wing 40 is in a first collapsed position, to keep the body 20 with a streamlined form during implantation. Details of such streamlining structures are particularly described in U.S. patent application Ser. No. 11/731,172, filed on Mar. 30, 2007, incorporated herein by reference in its entirety.

The body 20 includes a recess near the axle 24, and preferably on a side of the axle 24 opposite the distal end of the body 20, and on a distal side of the axle 24. This recess 26 defines an area which can accommodate receipt of the snap stay 50 (FIG. 7). The internal conduit 22 within the body 20 remains enclosed within the body 20, even adjacent this recess 26.

The body 20 includes a junction 28 at the proximal end. This junction 28 preferably allows for rigid and permanent attachment of the head 30 to the body 20. As an alternative, the head 30 and body 20 could be formed together as a single unit.

The body 20 could be formed of a variety of different materials including biocompatible metals such as stainless steel or titanium, or various other biocompatible materials including biocompatible plastics. The contour of the body 20 can be formed either by injection molding or casting procedures, or by machining procedures, or by some combination of such procedures, or other suitable manufacturing techniques.

Figure 2:
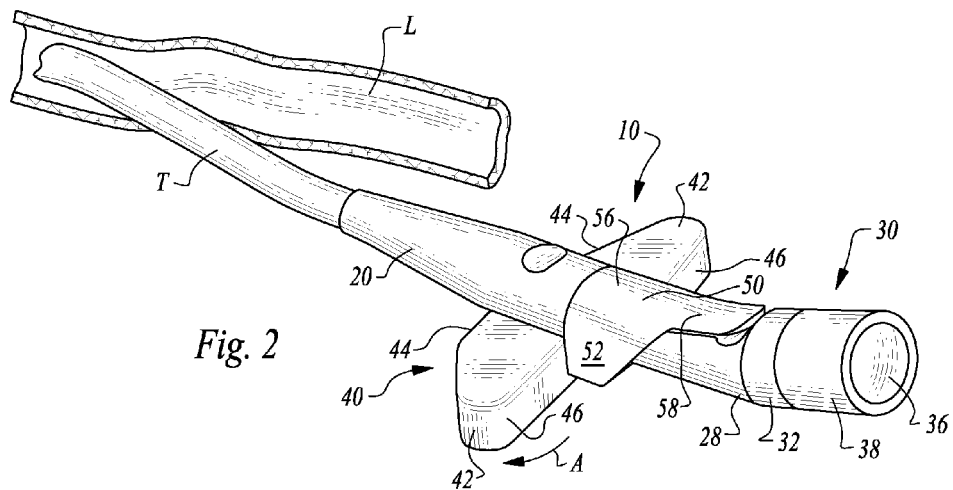
FIG. 2 is a perspective view of that which is shown in FIG. 1 and shown accessing a body lumen.
Figure 3:
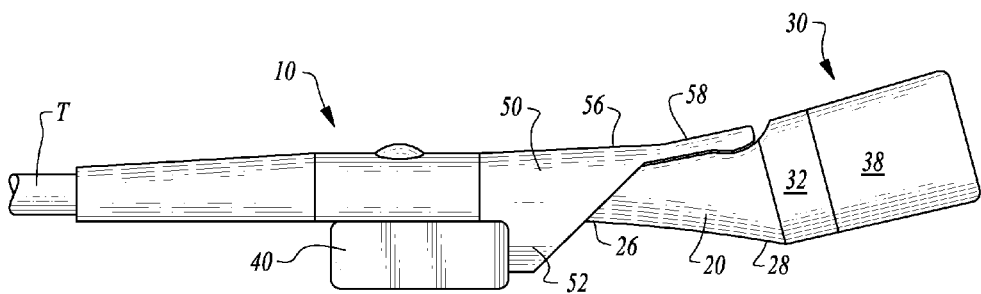
FIG. 3 is a side elevation view of that which is shown in FIG. 1.

With particular reference to FIGS. 1-3, details of the head 30 are described, according to the preferred embodiment. The head 30 is a rigid structure which is preferably securely and permanently attached to the body 20, or formed with the body 20 and which provides a portion of the port 10 to which a needle N can periodically interface with the port 10 for delivery of medications and other compositions into the patient. The head 30 preferably is a multi-part structure including a base 32 which couples to the body 20 directly. This base 32 is preferably generally cylindrical in form with a diameter similar to that of the body 20. Preferably, this base 32 has a slight angle upward in a direction opposite that of the axle 24, perhaps at an angle of 10° away from a long axis of the elongate body 20. The base 32 has a hollow interior defining a chamber 34. This chamber 34 is in fluid communication with the conduit 22 of the body 20 and an interior of the tube T.

A septum 36 is provided within the head 30 adjacent an end of the chamber 34 opposite the body 20. The septum 36 is preferably held adjacent the chamber 34 of the base 32 by a collar 38. This collar 38 has an aperture therein through which the septum 36 can be accessed, but which is restrained in size to keep the aperture from allowing the septum 36 to escape from the head 30 through the aperture. The collar 38 preferably puts the septum 36 under some degree of compression against the base 32. Thus, the septum 36 deforms slightly extending into the chamber 34 and is under compression to maximize the ability of the septum 36 to reseal after being penetrated by a needle N multiple times (FIG. 6). Preferably, the needle N is of a non-coring type to further enhance the reusability of the septum 36 for multiple penetrations by the needle N.

By causing the head 30 to be angled vertically upward slightly relative to a long axis of the body 20, the aperture in the collar 36, and hence the septum 36 can be more readily accessed by a needle N through the skin S (FIG. 6). Such accessibility can be further enhanced by following a method illustrated in FIG. 6. In particular, a medical professional would first utilize a finger F to palpate the skin S and feel for the location of the port 10. Once the port 10 has been found, the medical professional depresses the distal end of the body 20 (along arrow D of FIG. 6). The wing 40 at a midpoint of the port 10 acts as a form of fulcrum about which the entire body 20 of the port 10 can pivot. Thus, the head 30 is rotated upward (along arrow E of FIG. 6) pressing against the skin S. As the head 30 pushes against an underside of the skin S, the medical professional can see this abutment of the head 30 against the skin S and through appropriate training can direct the needle N slightly below this impact of the head 30 with the skin S for delivery of the needle N (along arrow F of FIG. 6) for accurate penetration of the septum 36.

With particular reference to FIGS. 1-3, 6 and 7, details of the wing 40 of the port 10 of this invention are described according to a preferred embodiment. The wing 40 provides a preferred form of stabilization structure for stabilizing the port 10 at the implantation site subcutaneously within the patient. This wing 40 has two positions including a first position and a second position. The second position places the wing 40 extending lateral to a long axis of the body 20 to resist rotation of the body 20 about a long axis thereof and assist in stabilizing the port 10. The first position is most preferably also attached to the body 20 but in an orientation having the wing 40 extending generally parallel with the long axis of the body 20 to be streamlined along with the elongate body 20, such as during implantation through a small incision in the skin S.

The wing 40 is preferably a rigid elongate structure which has a midpoint thereof rotatably coupled to the axle 24. The wing 40 extends from this midpoint to a pair of tips 42, spaced from each other by an overall length of the wing 40. Most preferably, the wing 40 is a simple elongate form between the tips 42 with no bends therein and with similar rounded corners on leading and trailing edges. Other optional containers for the wing 40 include those depicted herein. For instance, the wing 40 can have a forward side 44 for the wing 40 (after having been rotated to the second position) which is distinct from a rear side 46. In this embodiment, this forward side 44 is preferably more rounded than the rear side 46 and the rear side 46 is preferably substantially planar. In such a configuration, the wing 40 is more prone to deeper penetration into the patient than backing up backwards in the implantation site. Interior bodily structures resist movement of the port 10 deeper into the patient. With this biasing of the surfaces on the forward side 44 and rear side 46 of the wing 40, resistance is provided to the tendency of the port 10 to otherwise migrate slightly along a long axis of the elongate body 20 in a proximal direction.

Preferably, the wing 40 includes some means to restrain the wing 40 in the second position after the wing 40 has been rotated about the axle 24 from the first position aligned with the elongate body 20 to the second position extending lateral to the long axis of the elongate body 20. Such restraint could include sutures, especially if suture holes are provided on the body 20 and/or wing 30. Most preferably, the snap stay 50 is utilized to hold the wing 40 in the second position after the port 10 has been implanted.

In particular, and with particular reference to FIGS. 1-3 and 7, details of this snap stay 50 are described according to a preferred embodiment. The snap stay 50 is a substantially rigid structure but with a thin walled form that facilitates some flexibility thereof. The snap stay 50 includes fingers 52 which extend downwardly on opposite sides of a semi-cylindrical recess 54. A crown 56 joins the two fingers 52 together at an upper portion of the snap stay 50. An extension 58 extends in a posterior direction from the crown 56. The crown 56 is thin enough that the fingers 52 can flex slightly inwardly and outwardly toward and away from the semi-cylindrical recess 54 when forces are applied to the fingers 52.

The semi-cylindrical recess 54 is shaped similar to portions of the body 20 adjacent the recess 26 in the body 20. The semi-cylindrical recess 54 includes at least one rib thereon and preferably multiple ribs which abut portions of the body 20 adjacent the recess 26 when the snap stay 50 is pushed downwardly toward the recess 26, or downwardly and distally toward the recess 26 (along arrow B of FIG. 7). When these ribs snap past the portions of the body 20 adjacent the recess 26, the fingers 52 are first caused to move away from each other and then snap back together tightly to the portions of the body 20 adjacent the recess 26. The snap stay 50 is now tightly snapped to the body 20.

Forward portions of the fingers 52 are located directly adjacent the rear side 46 of the wing 50. Hence, the wing 40 is kept from rotating back to a first position, but is kept in a position after it has rotated (along arrow A of FIG. 2) from the first position to the second position. The snap stay 50 can cause rotation of the wing 40 (along arrow A of FIG. 2) by moving the snap stay 50 both downwardly and forward simultaneously, to cause rotation of the wing 40 and holding of the wing 40 in its rotated position after the snap stay 50 has snapped onto the body 20 adjacent the recess 26. As an alternative, the wing 40 can first be rotated to the desired position and then the snap stay 50 snapped onto the body 20 to keep the wing 40 in this final desired position.

When the port 10 is to be removed from the implantation site, the medical professional would first remove the snap stay 50 from the body 20. The wing 40 could then be allowed to rotate from the second position back to the first position to place the elongate body 20 in a streamlined form for removal out of a small incision.

Figure 4:
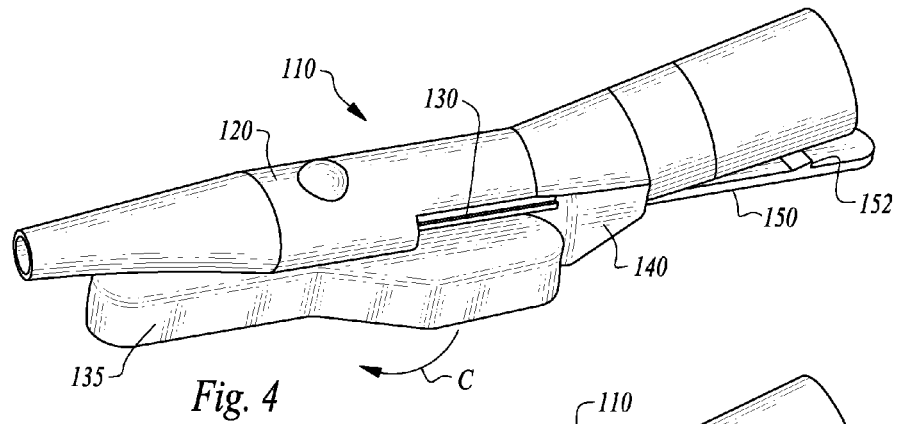
FIG. 4 is a perspective view of a first alternative port of this invention featuring a slide stay rather than the snap stay of the preferred embodiment.
Figure 5:
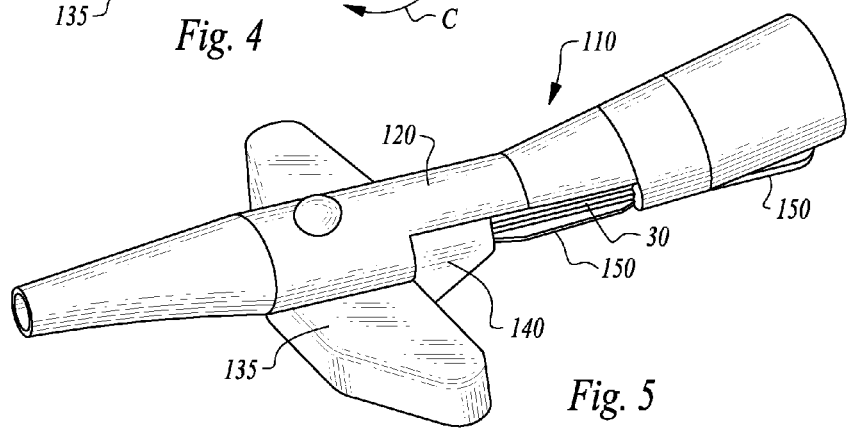
FIG. 5 is a perspective view similar to that which is shown in FIG. 4 but after rotation of a wing thereof to a second position from the first position shown in FIG. 4, and with the slide stay utilized to hold the wing in the second position.

With particular reference to FIGS. 4 and 5, details of a first alternative port 110 are described. This first alternative port 110 uniquely includes a slide stay 140 as an alternative to the snap stay 50 of the preferred embodiment. This alternative port 110 includes a body 120 with a rail 130 on a lower side thereof and on a proximal side thereof extending away from the location on the body 120 where a wing 135 is rotatably coupled to the body 120. The slide stay 120 rides on this rail 130 so that the slide stay 140 can slide along a longitudinal axis from the proximal end of the body 120 toward the distal end of the body 120. A tab 150 extends proximally from the slide stay 140. A medical professional can grip the tab 150 and push on the tab 150 to cause the slide stay 140 to slide from a first position (FIG. 4) which allows the wing 135 to be in a first collapsed position, to slide to a second position (FIG. 5) after the wing 135 has rotated (along arrow C of FIG. 4).

A tooth 152 on the tab 150 can engage a corresponding structure extending downward from the proximal end of the body 120 to hold the tab 150, and hence the slide stay 140 pressing against the wing 135, to keep the wing 135 in its deployed second position. In this embodiment, the wing 135 is configured so that it can be in its first collapsed position, and then when the slide stay 140 pushes on the wing 135 by sliding of the slide stay 140 along the rail 130 in a distal direction, the slide stay 140 causes the wing 135 to rotate along arrow C, from the first position to the second deployed position.

With particular reference to FIGS. 8-10, details of a second alternative port 210 are described. This second alternative port 210 is similar to the port 10 of the preferred embodiment except that the wing 240 is at least partially enclosed within a recess in the body 220. A head 230 is provided for access by a needle. The wing 24 can rotate out of the recess in the body 220 between the first collapsed position and the second deployed position similar to that described above with the port 10 of the preferred embodiment.

With such a recessed wing 240, a particularly highly streamlined form is provided for the elongate body 220. The wing 240 is preferably slightly angled so that tips of the wing 240 are not 180° opposed, but only approximately 165° opposed. A portion of the wing 240 on a proximal side when the wing 240 is in its first collapsed position acts as a form of trigger to initiate rotation of the wing 240 from the first collapsed position to the second deployed position. In particular, as implantation occurs, the portions of the wing 240 extending out of the recess (FIG. 9) can abut the skin S (FIG. 6) or other internal bodily structures. When such impact occurs, this portion of the wing that is on a proximal side of the wing and extending out of the recess is pushed into the recess, causing rotation of the wing 240 (about arrow G of FIG. 9). This in turn causes a distal portion of the wing 240 to pivot out of the recess. This distal portion of the wing then impacts internal bodily structures, causing further rotation of the wing 240 (about arrow G of FIG. 9) until the proximal end of the wing is now extending out the other side of the recess and a final static position is accomplished with the two ends of the wing extending laterally (FIG. 10). This embodiment is both highly streamlined and somewhat self-deploying for the wing 240.

With particular reference to FIGS. 11 and 12, details of a third alternative port 310 are described. This third alternative port 310 is similar to the port 10 of the preferred embodiment except that alternative head 330 and head 350 configurations are disclosed. Other portions of the body 320 and axle 325 and wing 340 are similar to those described herein with respect to the port 10 of the preferred embodiment. In particular, the head 330 of the embodiment of FIG. 11 includes a chamber 332 which is covered by a septum 335 captured against the chamber 332 by a collar 334. The collar 334 includes threads on an interior end thereof closest to the chamber 332. In this embodiment the chamber 332 is shown formed along with the body 320, rather than into a separate base as with the preferred embodiment. Furthermore, portions of the body 20 adjacent the collar 36 are threaded with threads matching those on an interior of the collar 334, so that the collar 334 can threadably attach to the body 20 until the septum 336 has been compressed and held tightly against the chamber 332.

In FIG. 12 a head 350 is disclosed similar to the head 330 of the embodiment of FIG. 11, except that the collar has been replaced with an extended portion of the body 320, that is contoured with a notch that allows the septum 356 to merely be snapped into this notch until the septum 356 is held tightly overlying the chamber 352. If it is required that the septum 356 be in a state of compression, the septum 356 could itself be provided in a modular structure that includes a compression collar pre-mounted on the septum 36, and then this compression collar snapped into the notch in the extension of the body 320 so that the modular septum 356 and associated collar would all be snapped into the proximal end of the body 320 and adjacent the chamber 350 to complete manufacture of the port 310 as illustrated in FIG. 12.

With particular reference to FIGS. 13 and 14, details of a fourth alternative port 410 are described. This fourth alternative port includes a body 420 and septum 430 which are similar to those described in U.S. patent application Ser. No. 11/651,770, filed on Jan. 9, 2007, incorporated herein by reference. Uniquely in this embodiment, rather than providing a rotating wing for stabilization of the port 410, a hole 430 is provided extending laterally through the body 420. This hole 430 is preferably threaded on at least a portion thereof. A rod stay 450 acts as a form of stabilizing ring to fit within this hole 430 and has threads 452 thereon which can mate with the hole threads. The rod stay 430 is provided separate from the body 420 of the port 410 initially. After the port 410 is at the implantation site, the medical professional positions the rod stay 450 within the hole 430 and finally threads the rod stay 450 with the rod stay 450 extending out of an opposite side of the hole 430 (along arrow H).

These threads could be on a midpoint of the rod stay 450 rather than on a tip, so that the rod stay 450 would extend laterally from the body 420 in both lateral directions. Furthermore, multiple such holes 430 could be provided for additional stabilization, such as on a proximal end and a distal end of the body 420. Removal of such a fourth alternative port 410 would occur by first removing the rod stay 450 to bring the port 410 back to a streamlined form, and then making an incision for removal of the other portions of the port 410 along a long axis thereof to minimize incision size and patient trauma.

Figure 15:
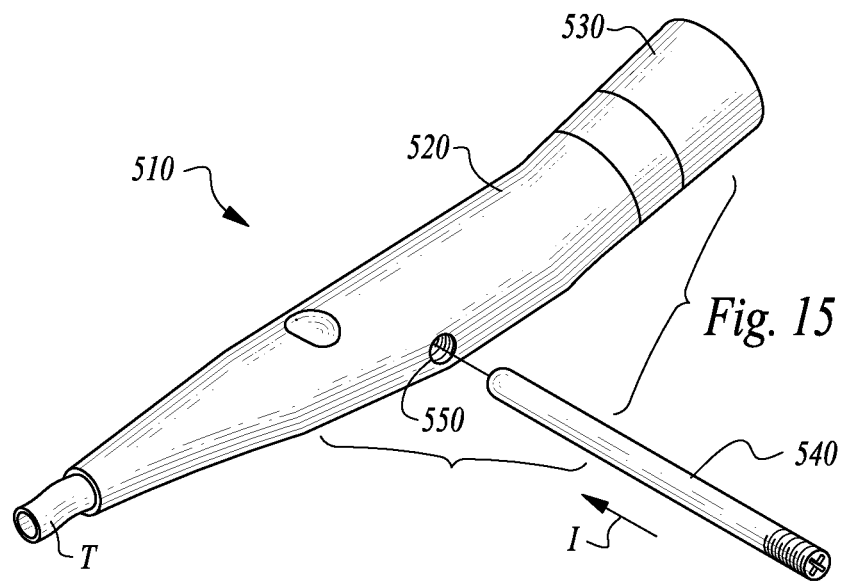
FIGS. 15 and 16 are perspective views of a fifth alternative port utilizing threaded wings on an elongated body style port.
Figure 16:
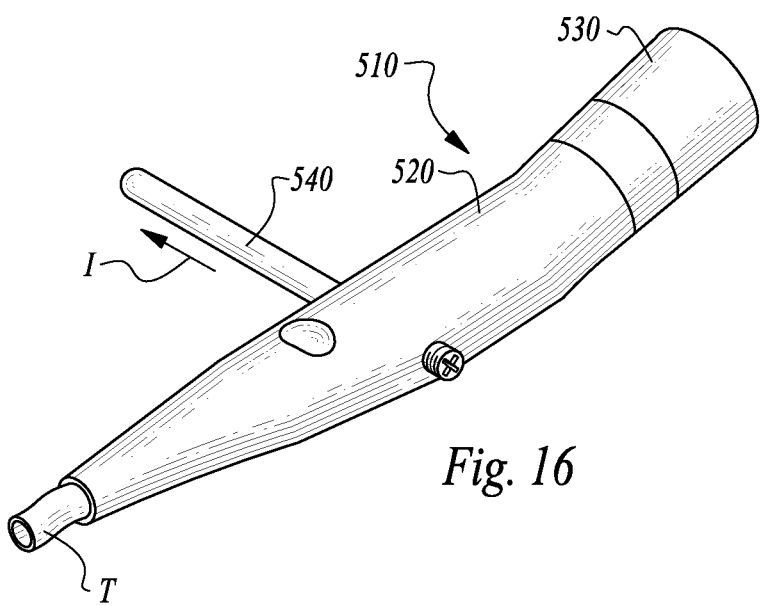

With particular reference to FIGS. 15 and 16, details of a fifth alternative port 510 are described. This fifth alternative port 510 includes a body 520 and head 530 similar to the body 20 and head 30 of the preferred embodiment port 10. Like the fourth embodiment of FIGS. 14 and 15, rather than providing a pivoting wing, the body 520 includes a hole 550 therein. A rod stay 540 is provided similar to the rod stay 450 of the embodiment of FIGS. 14 and 15. This rod stay 540 is passed into the hole 550 and utilizes threads to hold the rod stay in position after placement into the hole (along arrow I of FIGS. 15 and 16). As with the fourth embodiment of FIGS. 14 and 15, this rod stay 540 could be twice as long with the threads in the middle, so that it extends laterally in both directions away from the body 520. Also, if desired, multiple such holes 550 could be provided, such as for providing lateral stability both at a proximal end and a distal end of the body 520. This rod stay 540 provides a form of the wing of this invention for stabilization of the port 510.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A method for reliably and repeatedly accessing a body lumen through a subcutaneous port, the method including the steps of:
   identifying a port having an elongate body having a hollow interior extending between ends thereof, the ends including an outlet end and a proximal end opposite the outlet end, a head adjacent the proximal end of the body, the head including a chamber communicating with the hollow interior of the elongate body, a septum coupled to and in contact with the head and adjacent the chamber, the septum adapted to be penetrated by a needle passing through the skin, the elongate body adapted to be coupled, at least indirectly, to a body lumen, and a rigid wing affixed to and in contact with the elongate body and movably coupled to the elongate body, the wing having at least one tip, the tip having at least two positions including a first position and a second position relative to the body, the first position closer to the body than the second position;
   forming an incision adjacent where the port is desired to be implanted;
   inserting the port into the desired position subcutaneously;
   coupling a portion of the body spaced from the proximal end at least indirectly to the body lumen to be accessed; and
   moving the wing to adjust the position of the tip of the wing from the first position to the second position.

2. The method of claim 1 wherein said moving step includes rotating the rigid wing by a pivoting motion from the first position to the second position.

3. The method of claim 1 including the further steps of:
   pushing on a portion of the elongate body on a side of the wing opposite the head through the skin to cause portions of the elongate body on a side of the wing opposite where pushing is occurring to be moved toward the skin; and
   passing a needle through the skin and into the septum within the head of the elongate body after the head has been raised for easy access by said pushing step.

4. The method of claim 1 including the further step of manipulating a stay to abut the wing and resist rotation of the wing from the second position to the first position.

5. The method of claim 1 wherein said rotating step includes pivoting the wing about an axis non-parallel with a length of the elongate body.

6. A subcutaneous port for providing access to a body lumen, the port comprising in combination:
   an elongate body having a hollow interior extending between ends thereof;
   said ends including an outlet end and a proximal end opposite said outlet end;
   a head adjacent said proximal end of said body;
   said head including a chamber communicating with said hollow interior of said elongate body;
   a septum coupled to and in contact with said head and adjacent said chamber, said septum adapted to be penetrated by a needle passing through the skin;
   said elongate body adapted to be coupled, at least indirectly, to a body lumen; and
   a substantially rigid wing permanently affixed to and in contact with said elongate body and movably coupled to said elongate body, said wing having at least one tip, said tip having at least two positions including a first position and a second position relative to said body, said first position closer to said body than said second position.

7. The port of claim 6 wherein said elongate body includes said outlet end opposite said head, said outlet end adapted to be coupled, at least indirectly, to the body lumen.

8. The port of claim 6 wherein said wing has an elongate form of constant length and is located at an intermediate position between said ends of said elongate body.

9. The port of claim 8 wherein said wing is located closer to a middle of said elongate body than to either of said ends of said body.

10. The port of claim 8 wherein said wing is located on an underside of said elongate body adapted to be oriented most distant from skin beneath which the port is adapted to be implanted.

11. The port of claim 6 wherein said at least one wing is streamlined such that it passes more easily into a subcutaneous space than being pulled out of the subcutaneous space.

12. The port of claim 6 wherein said wing is adapted to rotate between said first position and said second position and a stay is adapted to be interposed against said wing to hold said wing in said second position.

13. A subcutaneous port for providing access to a body lumen, the port comprising in combination:
   an elongate body having a hollow interior extending between ends thereof;
   a head adjacent one of said ends of said body;
   said head including a chamber communicating with said hollow interior of said elongate body;
   a septum coupled to and in contact with said head and adjacent said chamber, said septum adapted to be penetrated by a needle passing through the skin;
   said elongate body adapted to be coupled, at least indirectly, to a body lumen;
   a substantially rigid wing permanently affixed to and in contact with said elongate body and movably coupled to said elongate body, said wing having at least one tip, said tip having at least two positions including a first position and a second position relative to said body, said first position closer to said body than said second position;
   wherein said wing is adapted to rotate between said first position and said second position and a stay is adapted to be interposed against said wing to hold said wing in said second position; and
   wherein said stay includes a snap stay adapted to snap onto said elongate body and surrounding at least a portion of said elongate body adjacent said wing with said snap stay including at least one downwardly extending finger adapted to abut a portion of the wing which resists the wing from rotating from said second position to said first position.

14. A subcutaneous port for providing access to a body lumen, the port comprising in combination:
an elongate body having a hollow interior extending between ends thereof;
a head adjacent one of said ends of said body;
said head including a chamber communicating with said hollow interior of said elongate body;
a septum coupled to and in contact with said head and adjacent said chamber, said septum adapted to be penetrated by a needle passing through the skin;
said elongate body adapted to be coupled, at least indirectly, to a body lumen;
a substantially rigid wing permanently affixed to and in contact with said elongate body and movably coupled to said elongate body, said wing having at least one tip, said tip having at least two positions including a first position and a second position relative to said body, said first position closer to said body than said second position;
wherein said wing is adapted to rotate between said first position and said second position and a stay is adapted to be interposed against said wing to hold said wing in said second position; and
wherein said stay includes a longitudinal guide rail on said elongate body and extending longitudinally on said elongate body with at least one end of said rail adjacent said wing, and a slide stay mounted on said rail and adapted to slide along said rail and into abutment with said wing to restrain said wing from rotating from said second position to said first position.

15. A subcutaneous port for providing access to a body lumen, the port comprising in combination:
an elongate body having a hollow interior extending between ends thereof;
a head adjacent one of said ends of said body;
said head including a chamber communicating with said hollow interior of said elongate body;
a septum coupled to and in contact with said head and adjacent said chamber, said septum adapted to be penetrated by a needle passing through the skin;
said elongate body adapted to be coupled, at least indirectly, to a body lumen;
a substantially rigid wing permanently affixed to and in contact with said elongate body and movably coupled to said elongate body, said wing having at least one tip, said tip having at least two positions including a first position and a second position relative to said body, said first position closer to said body than said second position;
wherein said body includes a hole passing laterally therethrough, said hole adapted to receive said wing in the form of a rod therein, said rod extending at least partially lateral to a long axis of said elongate body.

16. The port of claim 6 wherein said rigid wing is adapted to pivot relative to said elongate body, between said first position and said second position.

17. The port of claim 16 wherein said wing is adapted to pivot about an axis non-parallel with a length of said elongate body.

18. The port of claim 17 wherein said wing is adapted to pivot about an axis substantially perpendicular to said length of said elongate body.

19. The port of claim 6 wherein said rigid wing is elongate with a constant length.

20. A method for reliably and repeatedly accessing a body lumen through a subcutaneous port, the method including the steps of:
selecting a port having an elongate body having a hollow interior extending between ends thereof, the ends including an outlet end and a proximal end opposite the outlet end, a head adjacent the proximal end of the body, the head including a chamber communicating with the hollow interior of the elongate body, a septum coupled to and in contact with the head and adjacent the chamber, the septum adapted to be penetrated by a needle passing through the skin, the elongate body adapted to be coupled, at least indirectly, to a body lumen, and a rigid wing affixed to and in contact with the elongate body and movably coupled to the elongate body, the wing having at least one tip, the tip having at least two positions including a first position and a second position relative to the body, the first position closer to the body than the second position;
forming an incision adjacent where the port is desired to be implanted;
inserting the port into the desired position subcutaneously; and
coupling a portion of the body spaced from the proximal end at least indirectly to the body lumen to be accessed.

21. The method of claim 20 including the further step of rotating the rigid wing by a pivoting motion from the first position to the second position.

22. The method of claim 21 including the further step of manipulating a stay to abut the wing and resist rotation of the wing from the second position to the first position.

* * * * *